(12) United States Patent
Amiot et al.

(10) Patent No.: US 9,597,156 B2
(45) Date of Patent: Mar. 21, 2017

(54) BONE TRACKING WITH A GYROSCOPE SENSOR IN COMPUTER-ASSISTED SURGERY

(75) Inventors: Louis-Philippe Amiot, Hampstead (CA); Joel Zuhars, Warsaw, IN (US); Catherine Proulx, Verdun (CA); Mynam Valin, Laval (CA); Tin Nguyen, Laval (CA); Benoit Pelletier, Laval (CA); Karine Duval, Montréal (CA); Alain Richard, Lachine (CA); Rula Kiblawi, Dollard-des-Ormeaux (CA); Yannick Boutin, Montréal (CA)

(73) Assignee: ORTHOSOFT INC., Montreal, Quebec (CA)

( * ) Notice: Subject to any disclaimer, the term of this patent is extended or adjusted under 35 U.S.C. 154(b) by 641 days.

(21) Appl. No.: 12/846,934

(22) Filed: Jul. 30, 2010

(65) Prior Publication Data

US 2012/0029389 A1 Feb. 2, 2012

(51) Int. Cl.
*A61B 34/20* (2016.01)
*A61B 90/00* (2016.01)

(52) U.S. Cl.
CPC ...... *A61B 34/20* (2016.02); *A61B 2034/2048* (2016.02); *A61B 2090/3983* (2016.02)

(58) Field of Classification Search
CPC ........ A61B 19/5244; A61B 2019/5248; A61B 2019/5483
USPC ................ 600/407, 424, 431, 587, 592–593; 606/53, 86–89, 130
See application file for complete search history.

(56) References Cited

U.S. PATENT DOCUMENTS

| | | | |
|---|---|---|---|
| 5,611,353 A | 3/1997 | Dance et al. | |
| 6,381,858 B1* | 5/2002 | Shirasaka | 33/304 |
| 6,880,400 B1* | 4/2005 | Fogliatti et al. | 73/504.12 |
| 2002/0103610 A1* | 8/2002 | Bachmann et al. | 702/94 |
| 2003/0028196 A1* | 2/2003 | Bonutti | 606/87 |
| 2005/0143676 A1* | 6/2005 | De Guise et al. | 600/595 |
| 2006/0242096 A1 | 10/2006 | Ozaki et al. | |
| 2009/0247863 A1* | 10/2009 | Proulx et al. | 600/426 |
| 2009/0248044 A1 | 10/2009 | Amiot et al. | |
| 2010/0137869 A1 | 6/2010 | Borja et al. | |

OTHER PUBLICATIONS

PCT International Search Report of PCT/CA2010/001206.

* cited by examiner

*Primary Examiner* — Rene Towa
(74) *Attorney, Agent, or Firm* — Norton Rose Fulbright Canada LLP

(57) ABSTRACT

A system tracks an object in computer-assisted surgery. The system comprises a sensor unit secured to the femur. Gyroscopes on the sensor unit produce readings related to orientation data about three axes of rotation. A tracking unit receives the gyroscope readings. An axis calibrator on the tracking unit comprises a calculator for adding at least part of the gyroscope readings for specific movements of the object about a desired axis. An axis normalizer on the tracking unit determines an orientation of the desired axis with respect to the sensor unit from the added gyroscope readings. A tracking processor tracks the desired axis from the gyroscope readings. An interface displays orientation data for the object from a tracking of the desired axis. A method for tracking an object with a gyroscope sensor unit is also provided.

11 Claims, 5 Drawing Sheets

BONE TRACKING WITH A GYROSCOPE SENSOR IN COMPUTER-ASSISTED SURGERY

FIELD OF THE APPLICATION

The present application relates to tracking body parts such as bones in computer-assisted orthopedic surgery using gyroscopes and other microelectromechanical sensors (MEMS).

BACKGROUND OF THE ART

One of the essential steps in navigating a bone with MEMS sensors is to initially locate the bone relative to the sensors. For the femur, the orientation of the sensor relative to the lateral axis can be constrained mechanically, for instance, with claws inserted under the posterior condyles so that the sensor lateral axis is aligned with the lateral axis of the bone. However, the orientation of the sensor relative to the femoral mechanical axis is more complex, as one of the anatomical landmarks defining the axis, the femoral head, is hidden inside the hip.

In an optical navigation system, the femoral head is located by moving the femur and, assuming the pelvis is stable, finding the fixed pivot point around which the bone rotates. This relies on the optical sensor tracking the six degrees of freedom (DOF) of movement of the femur, i.e., 3DOF in position and 3DOF in orientation.

However, in a MEMS system, sensors do not automatically provide 6DOF. The 6DOF can be retrieved by integrating gyroscope and accelerometer readings—a standard technique called "dead reckoning"—but this technique is very sensitive to sensor errors and thus ill suited to low-cost sensors. Other gyroscope-based methods for retrieving the axis of the femur based on an axial rotation kinematic exist. However, such methods require a very specific and not natural leg motion, which might be difficult to apply and constrain.

SUMMARY OF THE APPLICATION

It is therefore an aim of the present disclosure to provide novel method and system for tracking bones using gyroscopes in computer-assisted surgery.

Therefore, in accordance with the present application, there is provided a system for tracking an object in computer-assisted surgery, comprising: a sensor unit adapted to be secured to the femur, the sensor unit comprising gyroscopes producing gyroscope readings related to orientation data about three axes of rotation; a tracking unit receiving the gyroscope readings and comprising an axis calibrator comprising a gyroscope reading calculator for adding at least a part of the gyroscope readings for specific movements of the object about a desired axis, and an axis normalizer for determining an orientation of the desired axis with respect to the sensor unit from the added gyroscope readings, and a tracking processor for subsequently tracking the desired axis from the gyroscope readings; and an interface for displaying orientation data for the object from a tracking of the desired axis.

Further in accordance with the present application, there is provided a method for tracking an object with a gyroscope sensor unit secured to the object, comprising: obtaining gyroscope readings for three axes of rotation during specific movements of the object about a desired axis; summing at least part of the gyroscope readings; determining an orientation of the desired axis with respect to the gyroscope sensor unit by normalizing the summed gyroscope readings; tracking the orientation of the desired axis of the object from the gyroscope readings; and displaying tracking data from the tracked orientation of the desired axis.

DESCRIPTION OF THE EXEMPLARY EMBODIMENTS

A gyroscope is a sensor which measures the instantaneous rotational velocity about an axis. If several gyroscope sensors are combined in a specific arrangement, a three-axis gyroscope sensor unit measuring the rotational velocity in x, y and z of a body is obtained. One property of gyroscopes is that if a three-axis gyroscope sensor unit rotates about a fixed axis, its output in x, y and z will be proportional to a direction of the rotation axis in the sensor coordinate system. The output represents a simultaneous rotation in x, y and z about a unit vector. Accordingly, three-axis gyroscope sensor units may be used to track axes of bones in computer-assisted surgery.

Figure 1:
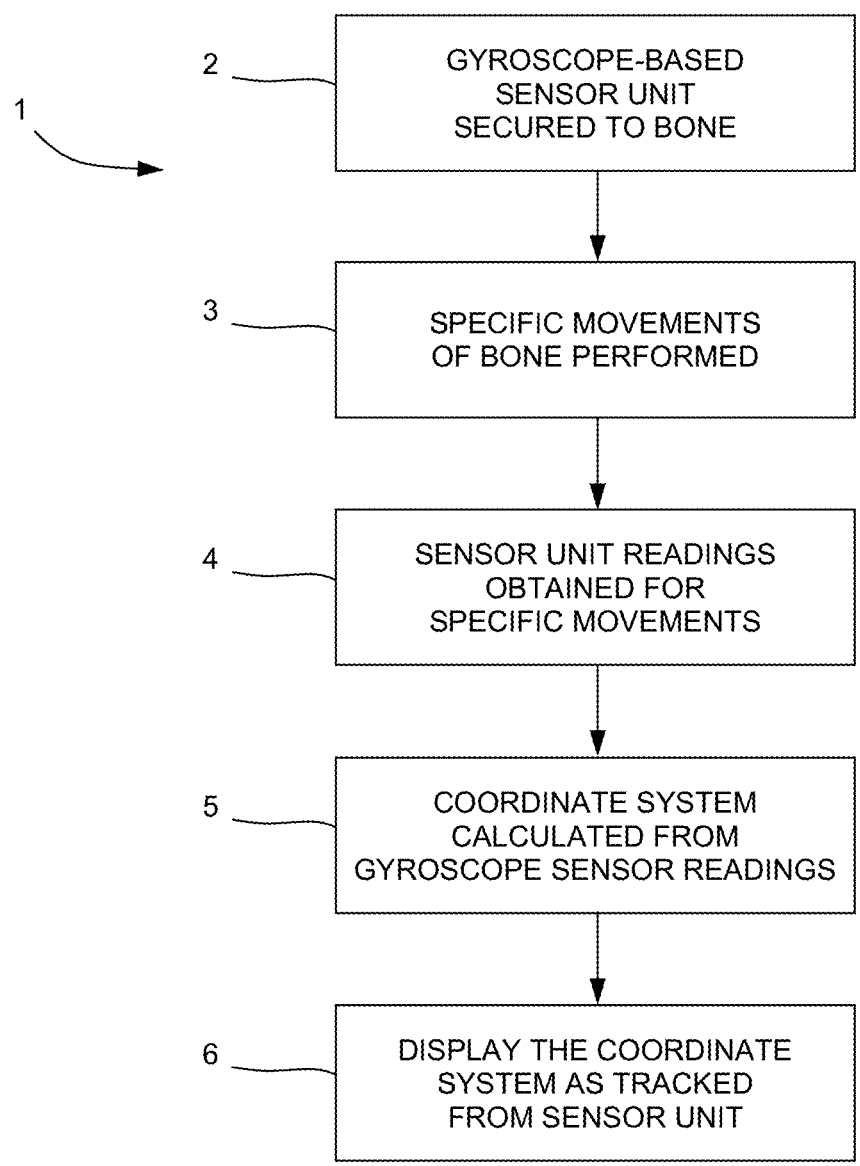
FIG. 1 is a flowchart of a method for tracking a bone with gyroscope sensor in computer-assisted surgery.

Referring to the drawings and more specifically to FIG. 1, there is illustrated a method 1 for tracking a bone in computer-assisted surgery. For clarity, the method 1 is described in an application related to the tracking of a femur. However, the method 1 can be used with some other bones and body parts, as well as bone models and on cadaver applications.

A femur registration will be performed to retrieve the coordinate system of the femur relative to the sensor unit, for subsequent tracking and navigation of the femur with the sensor unit. However, as the femoral head is hidden inside the hip socket, an external guide cannot be aligned with the mechanical axis of the femur, as it passes through the center of the femoral head. A rotation of the femur around its mechanical axis, tracked with the three-axis gyroscope sensor unit rigidly fixed to the bone, may be used to perform femur registration. The rotation axis, i.e., the mechanical axis, relative to the reference may then be calculated using properties of the three-axis gyroscope sensor unit. Moreover, if the sensor unit is aligned in correct alignment relative to the femur (e.g., alignment with the frontal plane), using mechanical or visual guides, the full coordinate system of the femur relative to the reference may be obtained.

According to step 2, the three-axis gyroscope sensor unit is rigidly secured to the bone. In the case of the femur, the sensor unit is typically secured adjacent to the knee end of the femur, while the femur may remain joined to the pelvis to form the hip joint. If it is desired to create and track a three-axis coordinate system, the sensor unit is positioned such that one of the axes of the sensor unit is aligned with an axis of the bone. In the femoral application, one of the axes of the sensor unit may be aligned with the lateral axis of the femur by using physiological landmarks of the femur.

In one embodiment, the sensor unit may be aligned visually with the epicondyles, the posterior condyles or trochlear groove. Mechanical guides (e.g., claws, visual markers, etc.) may also be provided with the sensor unit for the alignment thereof with these physiological landmarks. As an alternative, given motions may be performed to identify other axes, as described hereinafter.

According to step 3, specific movements of the bone must be performed. The specific movements are typically rotational motions of the bone about an axis that will be digitized, namely the mechanical axis in the case of the femur, or a longitudinal axis for other bones.

Figure 2:
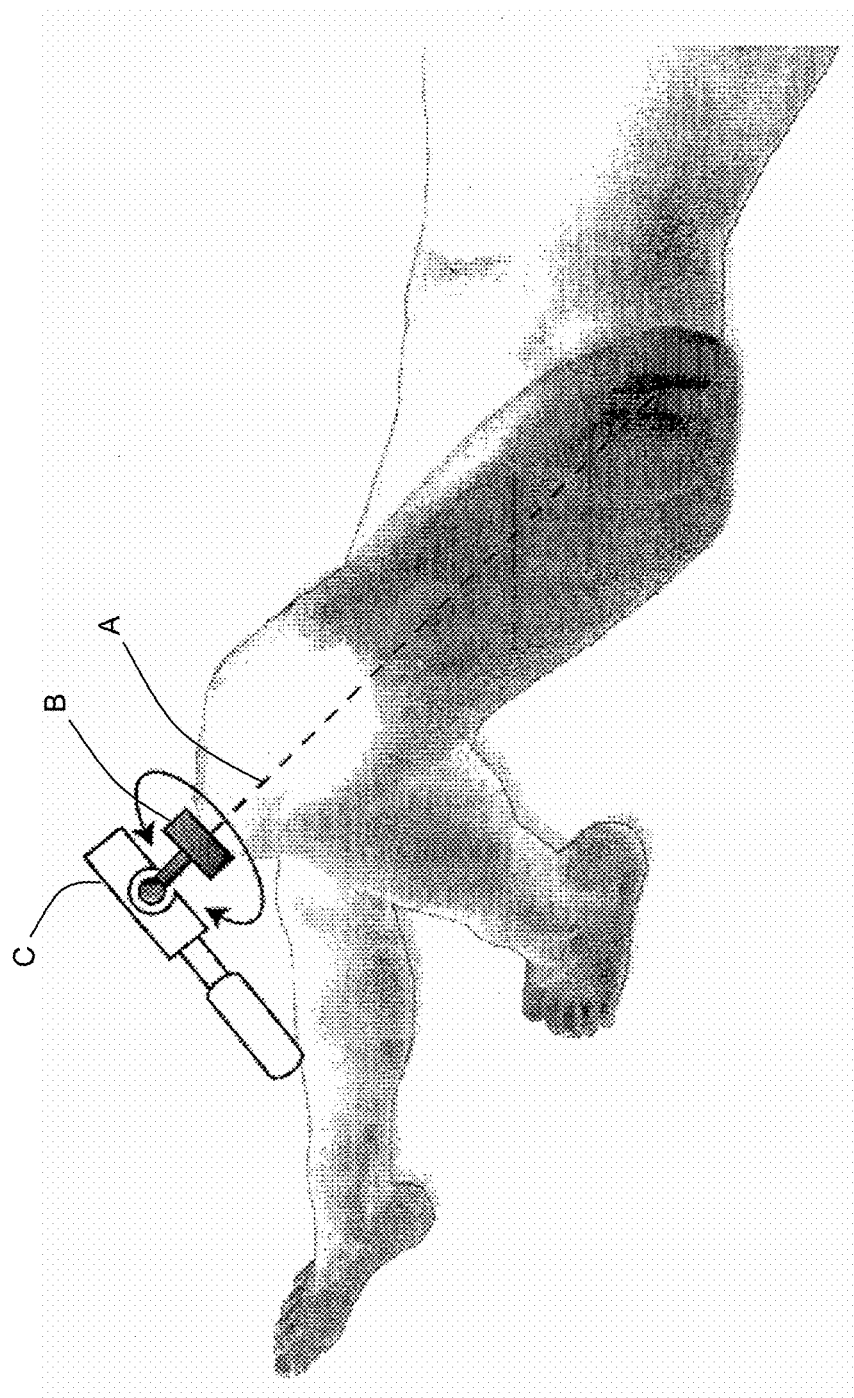
FIG. 2 is a schematic view of support instruments used to perform specific movements with a femur in accordance with the method of FIG. 1.

In the femoral application, the femoral head may remain in the acetabulum to define the hip joint. In an embodiment, motion of the distal end of the femur, namely at the knee end, is restricted to allow rotation about the mechanical axis A of the femur, as shown in FIG. 2. The specific movements in the case of the femur are back-and-forth oscillations about the mechanical axis A.

To obtain a stable reading from the three-axis gyroscope sensor unit, several back-and-forth motions are combined until a suitable total amplitude has been reached (e.g., 180°, which would correspond to three back-and-forth motions with 30° amplitude), or for a fixed duration of time (e.g., 15 seconds).

Figure 3:
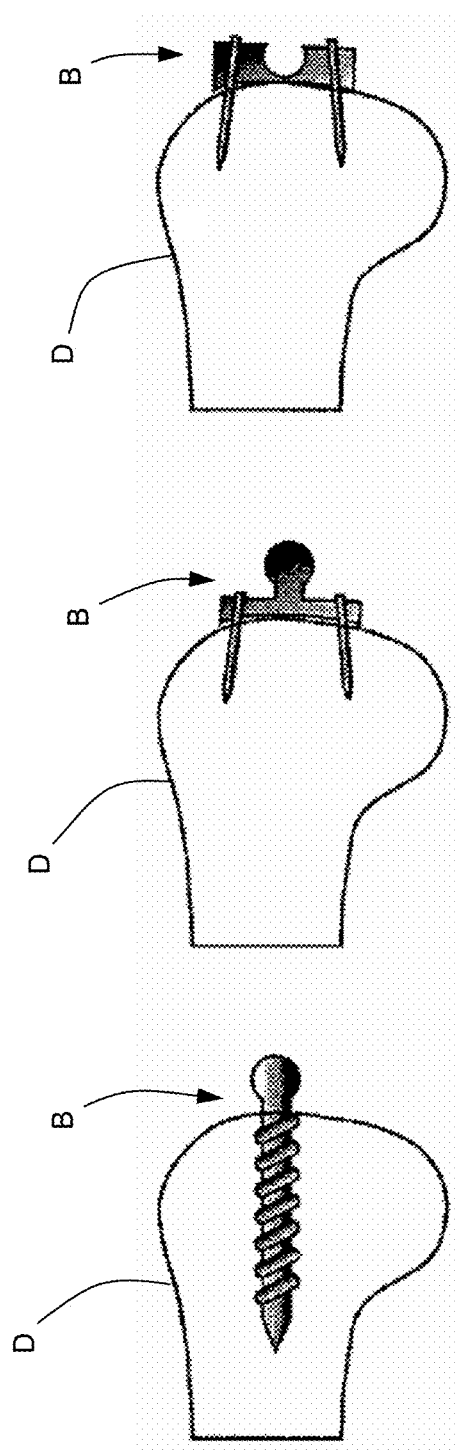
FIG. 3 are schematic views of femoral fixations used to perform the specific movements of the femur as in FIG. 2.

Referring concurrently to FIGS. 2 and 3, to restrict the motion of the femur about its mechanical axis A, a set of support tools may be used to support this step of the method. According to one embodiment, a femoral fixation B is secured to the femur, and is coupled to an external holder C. The resulting joint should allow the femur to rotate freely in three degrees of freedom (DOF), but not move in space. With both ends of the femur supported by fixed 3DOF joints, the femur is generally restricted to rotating about its mechanical axis.

In FIG. 3, there is illustrated three possible femoral fixations B, namely, (1) a screw with a ball joint head; (2) a distal reference, including a ball head; and (3) a distal reference, including a ball socket (in which case the external holder would have a ball head).

Referring to FIG. 2, the external holder C is selected in accordance with the type of femoral fixation B that is used. Options for the external holder C include non-exclusively (1) a handheld handle (as in FIG. 2); (2) a holder rigidly clamped to the operating table; and (3) a monopod/bipod/tripod structure, partially hand-stabilized by the surgeon, but which supports most of the weight of the leg. The specific movements of the femur may be performed as supported in a handheld manner. However, to support the weight of the leg and help guide the operator in performing the specific movements, the distal end of the femur may be held in place by the external support C, such as the monopod, or the structure clamped to the operating table.

Referring to FIG. 1, according to step 4, readings from the three-axis gyroscope sensor unit are obtained for the specific movements. The readings are an oscillating sequence of instantaneous rotational velocity values in the femur application.

In addition, the external holder C can be equipped with another sensor unit (e.g., accelerometers), so that unwanted motions of the knee end of the femur may be discriminate unstable readings from stable readings, to subsequently use only the stable readings of the sensor unit.

According to step 5, the orientation of the axis is calibrated with respect to the sensor unit. The calibration is performed by summing the sensor unit readings on the three axes for the rotation of the bone about its axis, and by normalizing the sum in x, y and z of the three-axis gyroscope sensor unit, to yield the desired axis. It may also be desired to filter out some of the values obtained in the gyroscope readings, as described below. In the case of the femoral application, the orientation of the mechanical axis is obtained with respect to the sensor unit.

If the readings from the three-axis gyroscope sensor unit are added after the back-and-forth motions, they would end up canceling each other since the rotation axis switches direction throughout the sequence. In order to compensate for the cancellation, the direction of the rotation is detected, and half the readings are inverted to obtain a consistent rotation axis.

To acquire the gyroscope readings during the oscillating sequence, the reading with the largest velocity magnitude is found. This measurement is normalized and defined as the reference axis $\vec{\gamma}$ for all measurements in the sequence. If the rotation axis is inverted relative to $\vec{\gamma}$, then the sensor unit readings are inverted.

If the readings from the sensor unit are summed for a small motion, small amounts of noise are continuously added, which may affect the rotation axis. To avoid this problem, the sequence in the sensor readings may be analyzed and portions where the readings are below the expected noise threshold on all three axes may be trimmed or discarded.

An outlier filtering scheme may be introduced to discard or exclude peaks of noise and irregular motions from the sum, to improve the stability. For instance, the outlier filtering scheme may be based on a RANSAC (i.e., random sample consensus) algorithm. The principle of the RANSAC algorithm is to pick a random subset of the data, fit a solution to this subset, and see how well the rest of the data agrees with this initial solution. If enough data is in consensus, the solution is considered good, and the data in disagreement is rejected as outlier. The remaining data is then used to compute a final best fit. If a consensus cannot be reached, the initial subset contained outliers, whereby the process is repeated with another sample until a maximum number of iterations is reached. The RANSAC algorithm is nondeterministic, since it relies on a random sample of the data to start the algorithm.

A gyroscope stability-detection algorithm may be used to reject the sequences where the motion is not consistent with a rotation about a fixed axis.

As mentioned previously, a sensor unit may be secured to the external holder C, whereby an accelerometer-based motion detection algorithm may be used to detect the stability of the knee end of the femur, and reject sequences where the knee end is not stable.

In the event that the sensor unit is aligned with another axis of the bone, a coordinate system comprising the two additional axes is obtained by setting a second one of the axes as being parallel to an axis of the sensor unit. The third axis is set as being in an orthogonal relation with the other two axes. For instance, if the sensor unit has an axis aligned with the lateral axis of the femur in the femoral application, the second one of the axes of the coordinate system is set to the axis of the sensor unit that is parallel to the lateral axis of the bone.

Other steps may be performed to define a three-axis coordinate system, such as performing given motions (e.g., flexion/extension). The flexion/extension of the knee is about the lateral axis of the femur, whereby the orientation of the lateral axis may be computed from the flexion/extension movement.

An extension of the method may allow the rotational point at the distal end of the femur to be offset from the real mechanical entry point.

According to step 6, information is displayed as a function of the tracking of the coordinate system. The information may be a representation of axes of the bone and of tools, models of bones and tools, values calculated as a function of the tracked coordinate system, visual displays on the tools signaling proper alignment, or any other appropriate data related to orthopedic surgery. The information is continuously updated during the tracking of the sensor unit.

Figure 4:
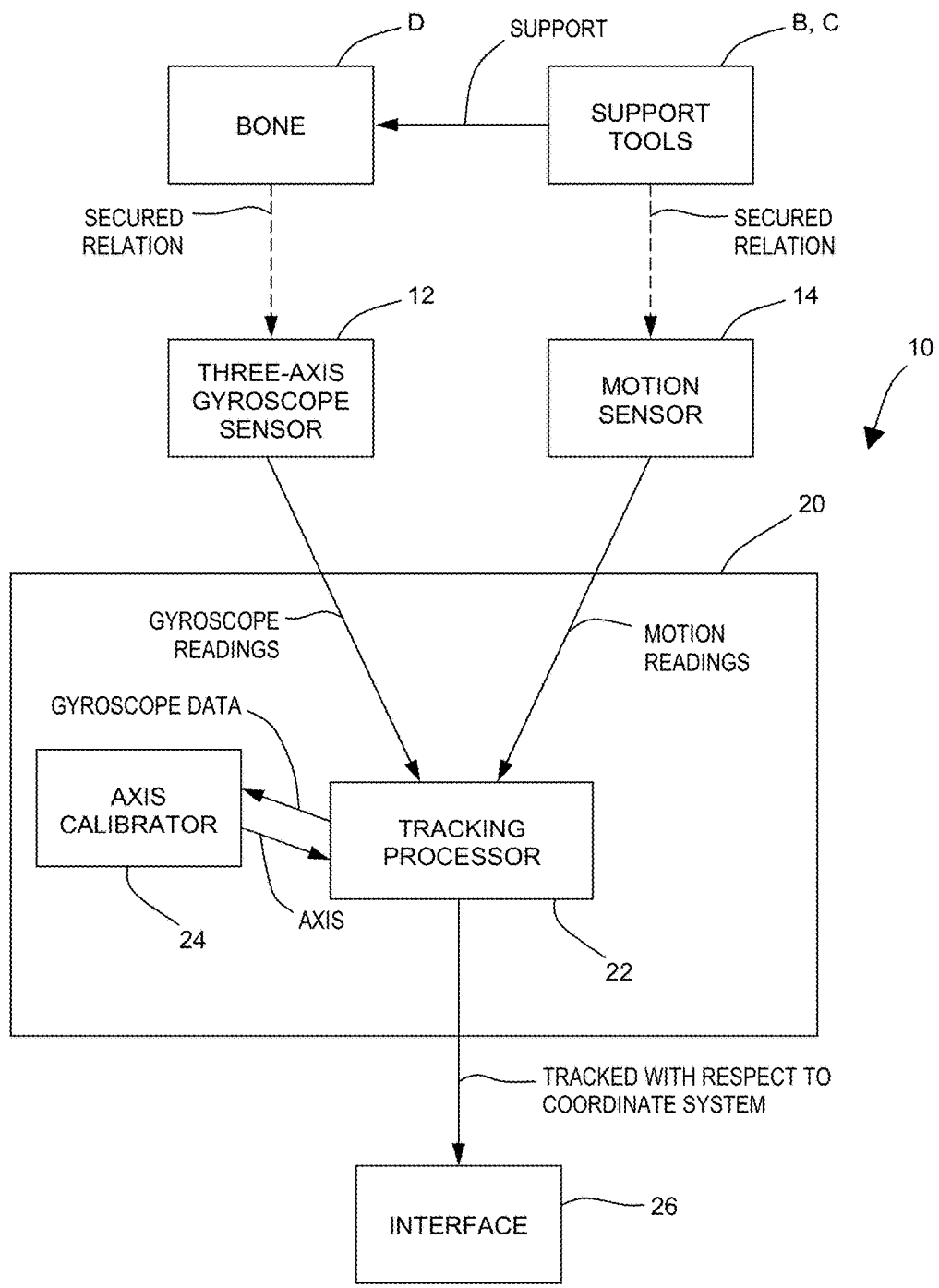
FIG. 4 is a block diagram of a system for tracking a bone with gyroscope sensor in computer-assisted surgery.

Referring to FIG. 4, a system 10 for tracking a bone with a gyroscope sensor unit is generally shown at 10, and comprises a three-axis gyroscope sensor unit 12 as rigidly fixed to a bone, for instance, as described for method 1 of FIG. 1. The gyroscope sensor unit 12 has gyroscopes arranged for three-axis tracking. A motion sensor 14, for instance, of the type featuring accelerometers or any other appropriate type of sensor, is in a secured relation with the support tools B, C.

A CAS tracking unit 20 receives readings from the sensor units 12 and 14 to define a coordinate system, i.e., an axis of a bone or a three-axis coordinate system for the bone. As mentioned previously, in the femoral application, the femoral coordinate system comprises at least the mechanical axis of the femur. The coordinate system is defined for subsequently tracking the bone from the readings of the sensor unit 12. The CAS tracking unit 20 comprises a processor and appropriate applications to define the coordinate system, for instance, as described by method 1. The application may be specifically a femoral application, or any other appropriate application.

The tracking unit 20 comprises a tracking processor 22, which receives gyroscope readings directly from the three-axis gyroscope sensor unit 12, and the motion readings from the motion sensor 14. The tracking processor 22 will convert the gyroscope readings to a tracking of the bone D with respect to the coordinate system that will be defined by an axis calibrator 24. Accordingly, prior to the tracking of the bone D and other tools during navigation, the axis must be calibrated by the axis calibrator 24. The information is then displayed using the interface 26.

Figure 5:
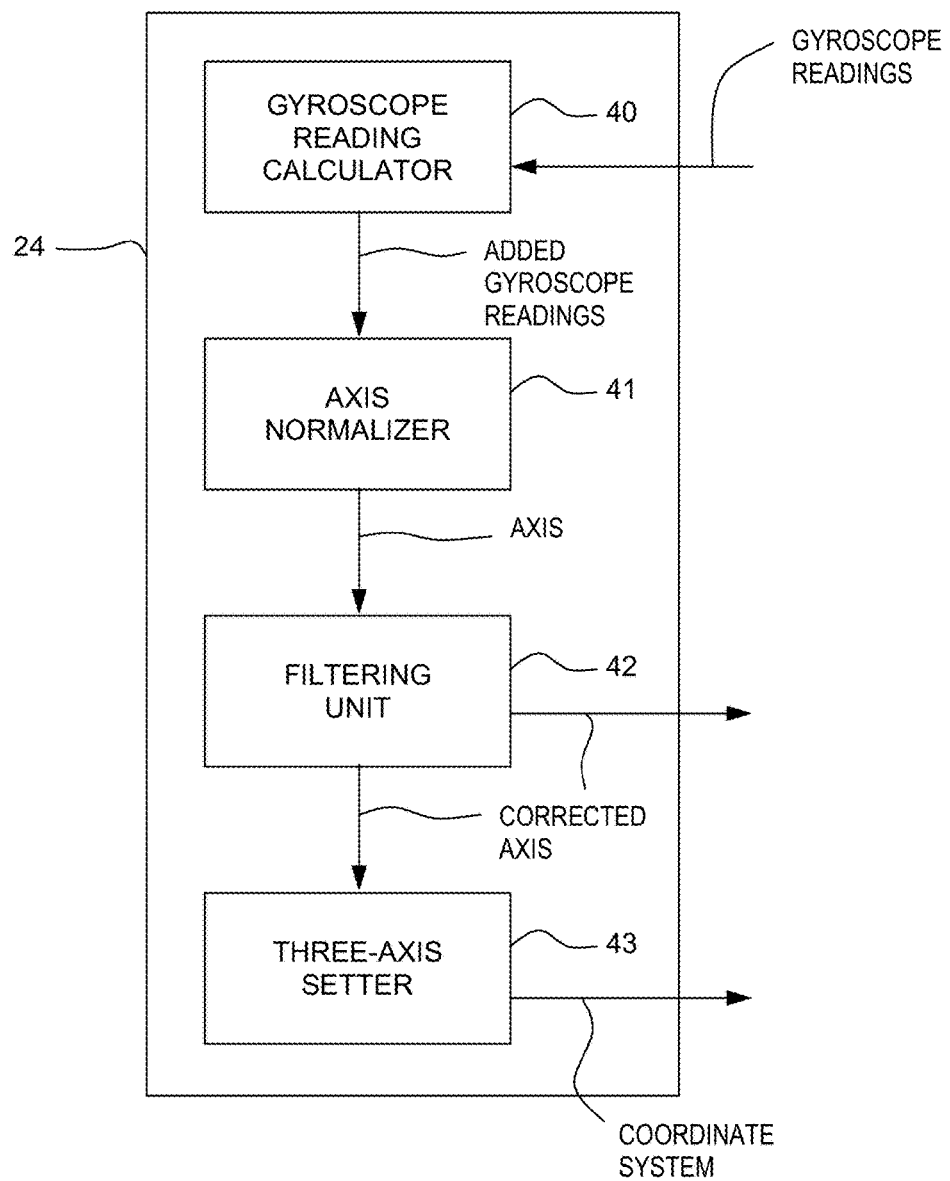
FIG. 5 is a block diagram of components of an axis calibrator of the system for tracking a bone with a gyroscope sensor of FIG. 4.

Referring to FIG. 5, the axis calibrator 24 is shown in greater detail, and comprises a gyroscope reading calculator 40 that will sum the various readings obtained from the gyroscope sensor unit 12, as described above for method 1. The total of the reading values are then normalized so as to define an axis by axis normalizer 41.

Some filtering is required, whereby the filtering unit 42 is provided to remove outlier points, or to cancel readings that were taken while the bone D was not fully stable, i.e., unstable readings. The motion sensor 14 provides a signal that the readings may not be used. The axis calibrator 24 may also comprise a three-axis setter by which two additional axes of a coordinate system will be set with respect to the axis previously defined. Accordingly, in addition to obtaining a given axis via the calculator 40, the normalizer 41 and optionally the filtering 42, the three-axis setter 43 adds the other two axes to form a three-axis coordinate system.

The information is displayed on the interface 26, which may be a monitor, as a function of the tracking of the coordinate system by the tracking processor 22, subsequent to the calibration of the axis and coordinate system by the axis calibrator 24. The information may be a representation of axes of the bone and of tools, models of bones and tools, values calculated as a function of the tracked coordinate system, visual displays on the tools signaling proper alignment, or any other appropriate data related to orthopedic surgery. The information is continuously updated during the tracking of the sensor unit in the navigation stages.

The invention claimed is:

1. A method for tracking a bone with a gyroscope sensor unit secured to the bone, comprising:
    obtaining, by a processor of a system for tracking a bone, gyroscope readings for three axes of rotation during specific movements of the bone about a desired axis, the specific movements being reciprocating movements of rotation of the bone about the desired axis with the bone and the desired axis both being fixed in position in space, the bone having an elongated shape and the desired axis being a longitudinal axis of the elongated shape;
    summing, by the processor, at least part of the gyroscope readings;
    determining, the processor, an orientation of the desired axis with respect to the gyroscope sensor unit by normalizing the summed gyroscope readings in the three axes;
    tracking, by the processor, the orientation of the desired axis of the bone from the gyroscope readings; and
    displaying, by a display of said system, tracking data from the tracked orientation of the desired axis of the bone.

2. The method according to claim 1, wherein summing at least part of the gyroscope readings comprises changing a direction of the gyroscope readings for all reciprocating movements in a first direction prior to summing.

3. The method according to claim 1, further comprising identifying, by the processor, any unstable gyroscope readings, and discarding the unstable gyroscope readings prior to determining the orientation of the desired axis.

4. The method according to claim 3, wherein identifying any unstable gyroscope readings comprises obtaining a motion sensor signal associated with at least some of the gyroscope readings.

5. The method according to claim 1, further comprising identifying and discarding, by the processor, outlier values from the gyroscope readings prior to determining the orientation of the desired axis.

6. The method according to claim 1, further comprising setting, by the processor, a second and a third axis to the desired axis to form a three-axis coordinate system.

7. The method according to claim 6, wherein setting a second axis comprises identifying a given axis of the sensor unit as the second axis.

8. The method according to claim 1, wherein the bone is a femur, and the desired axis is a mechanical axis of the femur.

9. The method according to claim 8, wherein the specific movements are rotations about the mechanical axis from the femur being constrained by a joint at a knee end, and by a hip joint at an opposite end.

10. The method according to claim 1, wherein the bone is a bone model or cadaver bone.

11. The method according to claim 1, further comprising displaying, by the display, information pertaining to an orientation of a tool relative to tracked orientation of the desired axis of the bone.

* * * * *